(12) United States Patent
Jeong

(10) Patent No.: US 11,864,575 B2
(45) Date of Patent: *Jan. 9, 2024

(54) COMPOSITION COMPRISING LOW TEMPERATURE WATER EXTRACT OF HIBISCUS MANIHOT FOR ANTI-OBESITY

(71) Applicant: Andong National University Industry-Academic Cooperation Foundation, Andong-si (KR)

(72) Inventor: Jin-Boo Jeong, Andong-si (KR)

(73) Assignee: Andong National University Industry-Academic Cooperation Foundation, Andong-si (KR)

( * ) Notice: Subject to any disclaimer, the term of this patent is extended or adjusted under 35 U.S.C. 154(b) by 10 days.

This patent is subject to a terminal disclaimer.

(21) Appl. No.: 17/670,524

(22) Filed: Feb. 14, 2022

(65) Prior Publication Data

US 2023/0189863 A1 Jun. 22, 2023

(30) Foreign Application Priority Data

Dec. 17, 2021 (KR) ........................ 10-2021-0181227

(51) Int. Cl.
*A61K 36/185* (2006.01)
*A23L 33/105* (2016.01)
*A61P 3/04* (2006.01)

(52) U.S. Cl.
CPC .......... *A23L 33/105* (2016.08); *A61K 36/185* (2013.01); *A61P 3/04* (2018.01)

(58) Field of Classification Search
None
See application file for complete search history.

(56) References Cited

FOREIGN PATENT DOCUMENTS

| CN | 101273999 B | * | 4/2011 |
| CN | 102526754 A | * | 7/2012 |
| KR | 10-2020-0120465 A | | 10/2020 |
| KR | 10-2176935 B1 | | 11/2020 |

OTHER PUBLICATIONS

Zhang (CN 1615947 A—English translation—2005).*

* cited by examiner

*Primary Examiner* — Susan Hoffman
(74) *Attorney, Agent, or Firm* — You & IP, LLC; Wansik You

(57) ABSTRACT

Provides is an anti-obesity composition, including a low-temperature Geumhwagyu extract as an active ingredient. The extract was obtained by adding Geumhwagyu to low-temperature water at 4 to 50° C. and extracting for 1 to 20 hours. The extract increases energy consumption through an increase in expression of adipose triglyceride lipase (ATGL) and hormone-sensitivity lipase (HSL), lipolysis through inhibition of expression of perilipin-1, and thermal generation through an increase in expression of uncoupling protein (UCP). In addition, the extract improves energy metabolism by increasing the expression of phospho-AMP-activated protein kinase (AMPK), inhibits lipid formation and accumulation of adipocytes by inhibiting cell growth of mature adipocytes, and shows anti-obesity activity, thereby being easily used as a pharmaceutical composition and healthy functional food for obesity.

1 Claim, 5 Drawing Sheets

COMPOSITION COMPRISING LOW TEMPERATURE WATER EXTRACT OF HIBISCUS MANIHOT FOR ANTI-OBESITY

CROSS REFERENCE TO RELATED APPLICATION

The present application claims priority to Korean Patent Application No. 10-2021-0181227, filed Dec. 17, 2021, the entire contents of which is incorporated herein for all purposes by this reference.

BACKGROUND OF THE INVENTION

1. Field of the Invention

The present disclosure relates to an anti-obesity composition including a low-temperature Geumhwagyu (*Hibiscus manihot* L.) extract as an active ingredient.

2. Description of the Related Art

Obesity refers to a medical condition in which body fat is excessively accumulated to the extent that it may have a negative effect on health. When the number of calories consumed from food exceeds the number of calories consumed through physical activity, it is stored as body fat. Obesity is when men have more than 25% body fat, and women have more than 30% body fat. Obesity is a condition in which fat is excessively accumulated in the body and is a risk factor that causes various adult diseases as well as appearance problems. Obesity is a cause of fatty liver, hyperlipidemia, osteoarthritis, cholelithiasis, hypertension, diabetes, and cardiovascular disease. In addition, it is known that prostate cancer, rectal cancer, and colorectal cancer are associated with obesity in men, and breast cancer, ovarian cancer, and uterine cancer are associated with obesity in women. In particular, obesity is a significant risk factor for heart disease, and it has been reported that obesity can significantly affect the structure and function of the heart. As it is known that the risk of heart failure increases rapidly with obesity in childhood, it is becoming an important problem in health care to solve obesity. The causes of obesity include diseases such as abnormalities in hypothalamic function energy metabolism and genetic factors, but most obesity is caused by lifestyle habits caused by excessive nutritional intake and a decrease in the amount of physical activity. In recent years, the incidence of obesity has continued to increase due to the increase in consumption of instant foods and lack of exercise due to western-style eating patterns and convenience of life. It is predicted that this trend will become more severe as time goes by. Recently, obesity has been socially recognized as a disease, and various pharmaceutical companies are focusing their efforts on developing drugs that treat obesity. The fat absorption inhibitor Xenical™ (Roche Pharmaceuticals, Switzerland) is one of the most used obesity treatments worldwide. Orlistat, a component of Xenical, combines with digested fat to suppress absorption in the intestine, thereby excreting some of the fat components during digesting. Other drugs developed include Riductil™ (Avot, USA) and Exolise™ (Atopharma, France), which enhance satiety. However, the commercialized drugs have reported side effects, including liver damage, gastrointestinal bleeding, pancreatitis, and kidney stones, and there is a risk of developing heart disease, respiratory disease, and nervous system diseases. Therefore, when using the currently commercialized anti-obesity treatments, it is required to develop a material having fewer side effects and excellent anti-obesity effects due to problems such as stability, as described above.

Geumhwagyu (*Hibiscus manihot* L.) is a medicinal plant with medicinal properties such as roots, stems, leaves, and flowers, and is a valuable medicinal herb that can only be obtained during the July-August harvest. Geumhwagyu is rich in collagen, which is effective for skin beauty, and contains a large number of effective ingredients such as palmitic acid, Gossypetin, oleic acid, betaine, and linolenic acid, so it is in the spotlight as a flower tea.

Accordingly, the present inventors completed the present disclosure by confirming that the Geumhwagyu extract has an anti-obesity effect while studying various physiological activities of the Geumhwagyu extract.

DOCUMENTS OF RELATED ART (Patent Document 0001) Korea Patent Application Publication No. 10-2020-0120465 (Title of the disclosure: Composition for preventing or treating liver damage caused by alcohol and for effectively relieving hangover, Applicant: Solgo Biomedical Co., Ltd., release date: Oct. 21, 2020).
(Patent Document 0002) Korea Patent No. 10-2176935 (Title of the disclosure: Cosmetic composition for wrinkle improvement and anti-inflammatory, Applicant: Jong-bok Kwak, date of registration: Nov. 4, 2020).

SUMMARY OF THE INVENTION

The objective of the present disclosure is to provide an anti-obesity composition, including a low-temperature Geumhwagyu (*Hibiscus manihot* L.) extract as an active ingredient.

The present disclosure relates to an anti-obesity composition, including a low-temperature Geumhwagyu (*Hibiscus manihot* L.) extract as an active ingredient.

The Geumhwagyu extract may be flowers, stems, leaves, or root extracts (extracts by part) of Geumhwagyu. In addition, the extract may be obtained by extracting Geumhwagyu using low-temperature water of 4 to 50° C. as a solvent. Preferably the extract may be a filtrate filtered after adding Geumhwagyu to low-temperature water of 4 to 50° C. and stirring at 4 to 50° C. for 1 to 20 hours. The filtrate may be dried and powdered and may be powdered through conventional drying methods such as freeze-drying, hot air drying, spray drying, and the like. The Geumhwagyu extract is preferably treated with an effective concentration of 1 to 200 µg/ml, more preferably 10 to 100 µg/ml, most preferably 10 to 50 µg/ml, at least 10 to 30 µg/ml to be used as an anti-obesity composition. The extract may have a lipid accumulation inhibitory effect of 75 to 90%, more preferably 81% or more (81 to 90%) at 30 µg/ml, 35% or more, more preferably 21% or more at 10 µg/ml. When preparing the extract, if the temperature exceeds 50° C., the lipid accumulation inhibitory effect may not be well expressed. Even if the extraction time exceeds 20 hours, the lipid accumulation inhibitory effect appears, but the effect is the best within 20 hours.

In the present disclosure, a process of sterilizing may be performed after extracting Geumhwagyu using low-temperature water. At this time, the sterilization application time is preferably 10 minutes to 1 hour or less at 80 to 130° C. Even if the extract extracted at a low temperature is sterilized at a high temperature, the efficacy of the extract can be maintained. Therefore, this proves that various oil-soluble substances in Geumhwagyu are not extracted well in hot water and are better extracted in low-temperature water, but once extracted, their activity does not change with a change in temperature. Therefore, on the contrary, even if the pasteurization method after extraction at 80 to 130° C. is applied, it is not easy to extract Geumhwagyu from hot water, so the desired lipid accumulation inhibitory effect in the present disclosure may not be expressed.

On the other hand, in the present disclosure, although Geumhwagyu may be extracted using an organic solvent, the extract obtained using low-temperature water of 4 to 50° C. suggests the highest lipid accumulation inhibition effect. In the present disclosure, the low-temperature extract for each part of Geumhwagyu is also called Geumhwagyu extract.

In addition, as a conventional method in the art, after dissolving the low-temperature Geumhwagyu extract in water, the Geumhwagyu extract may be further fractionated using at least one solvent selected from the group consisting of n-hexane, methylene chloride, acetone, chloroform, ethyl acetate, and n-butanol to prepare a fraction. In another method, after suspension by adding water to the low-temperature Geumhwagyu extract, preferably 1 to 1000 times the weight of the Geumhwagyu extract, more preferably 1 to 500 times, and most preferably 1 to 50 times the weight of the Geumhwagyu extract, and then the Geumhwagyu extract may be prepared as a Geumhwagyu fraction obtained by adding a solvent selected from the group consisting of hexane, chloroform, ethyl acetate, and butanol to the suspension. The Geumhwagyu fraction may preferably be: a hexane layer concentrate obtained by suspending the low-temperature extract of Geumhwagyu in water and mixing it with hexane; a chloroform layer concentrate obtained by mixing chloroform with the residue (water layer) remaining after removing the hexane layer; an ethyl acetate layer concentrate obtained by mixing ethyl acetate with the residue (water layer) remaining after removing the chloroform layer; a butanol layer concentrate obtained by mixing butanol with the residue (water layer) remaining after removing the ethyl acetate layer; or a remaining residue (water layer) concentrate after removing the butanol layer. On the other hand, other fractionation conditions are not limited, but a suspension may be prepared by adding water of 1 to 50 times the weight of the Geumhwagyu extract to the Geumhwagyu extract, and then fractionated by adding a solvent selected from the group consisting of hexane, chloroform, ethyl acetate, and butanol equivalent to the water. In addition, even when chloroform is added to the remaining residue after removing the hexane layer, when ethyl acetate is added to the remaining residue after removing the chloroform layer, and when butanol is added to the remaining residue after removing ethyl acetate, and also even when it is performed in stages, each solvent (chloroform, ethyl acetate, or butanol) equivalent to the residue can be sequentially added and fractionated.

As an apparatus for extracting the Geumhwagyu extract or fractions, a conventional extraction apparatus, an ultrasonic crushing extractor, or a fractionator may be used. The thus-prepared Geumhwagyu extract may be dried with hot air, dried under reduced pressure, or freeze-dried to remove the solvent. In addition, the Geumhwagyu extract or fraction may be purified and used using column chromatography. The low-temperature Geumhwagyu extract may be used by fractioning or purifying using the known method alone or a suitably combined method used for separation and extraction of plant components, such as extraction by an organic solvent (alcohol, ether, acetone, etc.), distribution of hexane, and water, and method by column chromatography, according to the commercial method. The chromatography may be selected from silica gel column chromatography, LH-20 column chromatography, ion exchange resin chromatography, medium pressure liquid chromatography, thin-layer chromatography (TLC), silica gel vacuum liquid chromatography, and high-performance liquid chromatography.

In addition, the present disclosure provides a pharmaceutical composition for anti-obesity containing Geumhwagyu extract. The Geumhwagyu extract may be added to the pharmaceutical composition of the present disclosure in an amount of 0.001% to 100% by weight.

The pharmaceutical composition may be formed in the form of oral formulations such as powders, granules, tablets, capsules, suspensions, emulsions, syrups, aerosols, etc., external preparations, suppositories, and sterile injection solutions according to conventional methods, respectively. Carriers, excipients, and diluents that may be included in the pharmaceutical composition may include lactose, dextrose, sucrose, sorbitol, mannitol, xylitol, erythritol, maltitol, starch, acacia gum, alginate, gelatin, calcium phosphate, calcium silicate, cellulose, methylcellulose, microcrystalline cellulose, polyvinyl pyrrolidone, water, methyl hydroxybenzoate, propyl hydroxybenzoate, talc, magnesium stearate, and mineral oil. In the case of formulation, it is prepared using commonly used fillers, extenders, binders, wetting agents, disintegrants, diluents such as surfactants or excipients. Solid preparations for oral administration include tablets, pills, powders, granules, capsules, etc. These solid preparations are prepared by mixing at least one excipient, such as starch, calcium carbonate, sucrose or lactose, gelatin, etc. In addition to simple excipients, lubricants such as magnesium stearate and talc are also used. Liquid formulations for oral administration include suspensions, solutions, emulsions, syrups, etc. In addition to water and liquid paraffin, which are commonly used simple diluents, various excipients, for example, wetting agents, sweeteners, fragrances, preservatives, etc., may be included. Formulations for parenteral administration include sterile aqueous solutions, non-aqueous solutions, suspensions, emulsions, freeze-dried preparations, and suppositories. Vegetable oils such as propylene glycol, polyethylene glycol, and olive oil and injectable esters such as ethyl oleate may be used as non-aqueous solvents and suspensions. As the base of the suppository, Witepsol, Macrogol, Tween 61, cacao butter, laurin butter, glycerogelatin, etc., can be used.

The dosage of the pharmaceutical composition of the present disclosure will vary depending on the age, gender, weight, specific disease or pathology to be treated, severity of the disease or pathology to be treated, the route of administration, and the prescription. Dosage determination based on these factors is within the level of those of ordinary skilled in the art. Generally, dosages range from 0.01 mg/kg/day to approximately 2000 mg/kg/day. A more preferred dosage is 1 mg/kg/day to 500 mg/kg/day. Administration may be administered once a day or may be administered in several divided doses. The above dosage does not limit the scope of the present disclosure in any way.

The pharmaceutical composition of the present disclosure may be administered to mammals such as mice, livestock, and humans by various routes. Any mode of administration can be envisaged, for example, by oral, rectal or intravenous, intramuscular, subcutaneous, intrauterine dural, or intracerebrovascular injection. Since the extract of the present disclosure has almost no toxicity and side effects, it is a drug that can be safely used even when taken for a long time for prevention.

In addition, the present disclosure provides healthy functional food for anti-obesity, including a Geumhwagyu extract and a food additive that is acceptable in terms of food. The Geumhwagyu extract may be added to the health functional food of the present disclosure in an amount of 0.001% to 100% by weight. The healthy functional food of the present disclosure includes the form of tablets, capsules, pills, or liquids, and the food to which the extract of the present disclosure can be added includes, for example, various drinks, meat, sausage, bread, candy, snacks, noodles, ice cream, dairy products, soups, ionized beverages, beverages, alcoholic beverages, gum, tea, and vitamin complexes.

The present disclosure relates to an anti-obesity composition, including a low-temperature Geumhwagyu extract as an active ingredient. The extract was obtained by adding Geumhwagyu to low-temperature water at 4 to 50° C. and extracting for 1 to 20 hours. The extract increases energy consumption by increasing the expression of adipose triglyceride lipase (ATGL) and hormone-sensitive lipase (HSL), fatty decomposition through inhibition of the expression of perilipin-1, and thermal generation through the expression of uncoupling protein (UCP). In addition, the extract has an effect of enhancing energy metabolism by increasing the phosphorylated phospho-AMP-activated protein kinase (AMPK). The extract inhibits the cell growth of mature adipocytes to suppress the lipid formation and accumulation of adipocytes, thereby showing anti-obesity activity. The extract may be easily used as a pharmaceutical composition for preventing or improving obesity and as a healthy functional food.

DESCRIPTION OF THE PREFERRED EMBODIMENTS

Figure 1:
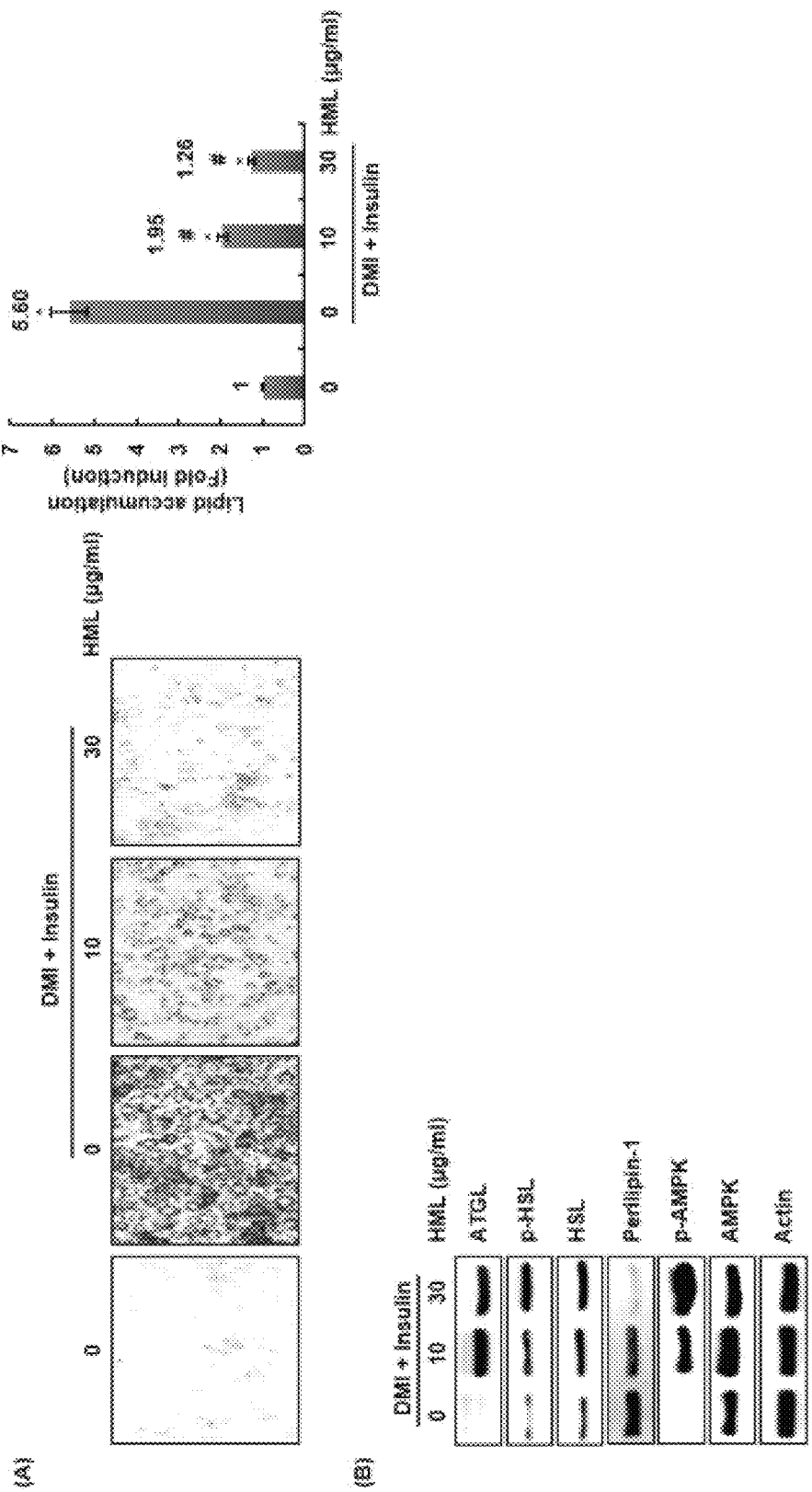
FIG. 1 is a cell image of lipid accumulation according to the Oil Red O experiment using a low-temperature extract of Geumhwagyu leaf (HML), the absorbance result of the cell eluate, and an image of Western blot results showing increased expression of lipolysis-related proteins ATGL (adipose triglyceride lipase) and HSL (hormone-sensitive lipase), inhibition of Perilipin-1 expression, increased expression of UCP (uncoupling protein), increased expression of phosphorylated phospho-AMP-activated protein kinase (AMPK), which is a thermogenic protein.

Hereinafter, preferred embodiments of the present disclosure will be described in detail.

However, the present disclosure is not limited to the embodiments described herein and may be embodied in other forms. Rather, it is provided so that this disclosure will be thorough and complete and will fully convey the spirit of the disclosure to those skilled in the art.

Example 1: Preparation of Geumhwagyu Extract

Geumhwagyu leaf extract was prepared through the following process. First, each of the leaves was washed and dried with distilled water, and then 20 times the volume of water was added to 10 g of dry pulverized material, and then immersed according to conditions with a temperature difference of 1 to 20 hours at 4 to 100° C. to obtain each leaf extract, respectively. Thereafter, the extract was filtered and then lyophilized to obtain a final Geumhwagyu leaf extract (HML).

Example 2: Cytotoxicity Assay

In order to check whether the Geumhwagyu extract of the present disclosure obtained in Example 1 is toxic to cells, cytotoxicity was analyzed in vitro.

To this end, 3T3-L1, a pre-adipocyte, was purchased from KCLB and used. After the cells were aliquoted in a cell culture flask, 10% fetal bovine serum (FBS) and 1% penicillin-streptomycin (10,000 U/ml) were added to the DMEM medium and cultured and used in an incubator maintained at 37° C., 5% CO2, and 95% humidity conditions. For cytotoxicity evaluation, the MTT assay was used, in which the method uses a principle that dehydrogenases in mitochondria of cells with intact metabolic processes reduce yellow water-soluble tetrazolium salt [3-(4,5-dimethylthiazol-2-yl)-2-5-diphenyltetrazolium bromide] (MTT) to non-soluble dark purple MTT formazan crystals. The crystal was evaluated for cytotoxicity by measuring absorbance at an appropriate wavelength (mainly 500-600 nm).

First, 3T3-L1 cells were aliquoted into 96 wells at a 1×105 cells/well concentration and then cultured for 24 hours. Then, each part of the extract of Geumhwagyu prepared in Example 1 was treated at a concentration of 0, 50, 100, and 200 μg/mL, respectively, and after incubation for 24 hours, MTT at a concentration of 1 mg/mL was added and incubated at 37° C. for 2 hours. After the reaction, DMSO (dimethyl sulfoxide) was added, and absorbance was measured at 570 nm using a microplate reader.

As a result of the analysis, it was confirmed that all Geumhwagyu extracts had no cytotoxicity, and then the following experiment was performed (graph not attached).

Example 3: Lipid Formation and Accumulation Inhibitory Activity of Geumhwagyu Extract 313-L1 cells, which are pre-adipocytes, were aliquoted into 24 wells at a 1×105 cells/well concentration and cultured for 3 days and then differentiated with the DMI medium (adipogenic medium). As the MDI medium, 10% FBS/DMEM treated with 0.5 mM of IBMX, 1 μM dexamethasone, and 1 μg/ml insulin was used. This time point was regarded as day 0 of differentiation, and after 2 days of differentiation, 1 μg/ml of insulin medium was replaced, and after 2 days of culture, 10% FBS medium was replaced and maintained for up to 8 days. Geumhwagyu extract was added on day 0 of differentiation and treated for 8 days. After 8 days of differentiation, the degree of differentiation of adipocytes and the degree of inhibition of differentiation by Geumhwagyu extract were analyzed through Oil Red O staining. After adipocyte differentiation and Geumhwagyu extract treatment were completed, cells were washed with 1× phosphate-buffered saline (PBS), and then 10% (w/v) formalin was added and fixed at room temperature for 1 hour. After removing the formalin and washing each well in which the cells were cultured with 60% (v/v) isopropanol, the isopropanol was completely blown away from the hood. Oil red 0 solution was added to the dried cell culture wells, left for 10 minutes, washed with distilled water, and adipocyte differentiation was confirmed by microscopic imaging. The stained cell culture wells were dissolved in 100% isopropanol, and absorbance was measured at 500 nm. The triglyceride (TG) amount in adipocytes was measured using a commercially available TG assay kit (Triglyceride Assay Kit Quantification, ab65336).

Each experimental result is described in FIGS. 1 to 5.

FIG. 1 shows an image of Western blot results showing the increased expression of Adipose triglyceride lipase (ATGL) and Hormone-sensitive lipase (HSL) and expression suppression of Perilipin-1, which are lipolysis-related proteins of an extract of Geumhwagyu leaf (HML) obtained by extraction at 40° C. for 20 hours, increased expression of UCP (uncoupling protein), a thermogenic protein, and increased expression of phosphorylated AMP-activated protein kinase (p-AMPK) related to energy metabolism enhancement. Referring to FIG. 1, it may be confirmed that the Geumhwagyu leaf extract has the most excellent lipid accumulation inhibitory effect when extracted at a low temperature.

Next, the effects of the Geumhwagyu leaf extract were compared once again with the root, stem, and flower extracts. As a result, as shown in Table 1 below, it can be seen that, like the leaf extract, the extracts for different parts also have very excellent lipid accumulation inhibitory effects.

TABLE 1

| | Lipid accumulation (fold) | | |
|---|---|---|---|
| Extract (40° C. water, 20 hours) | Extract treatment concentration 0 µg/ml | Extract treatment concentration 10 µg/ml | Extract treatment concentration 30 µg/ml |
| Fat differentiation induction + Geumhwagyu root extract | 1.00 | 0.29 | 0.19 |
| Fat differentiation induction + Geumhwagyu Stem Extract | 1.00 | 0.26 | 0.21 |
| Fat differentiation induction + Geumhwagyu flower extract | 1.00 | 0.21 | 0.14 |
| Fat differentiation induction + Geumhwagyu leaf extract | 1.00 | 0.25 | 0.17 |

Figure 2:
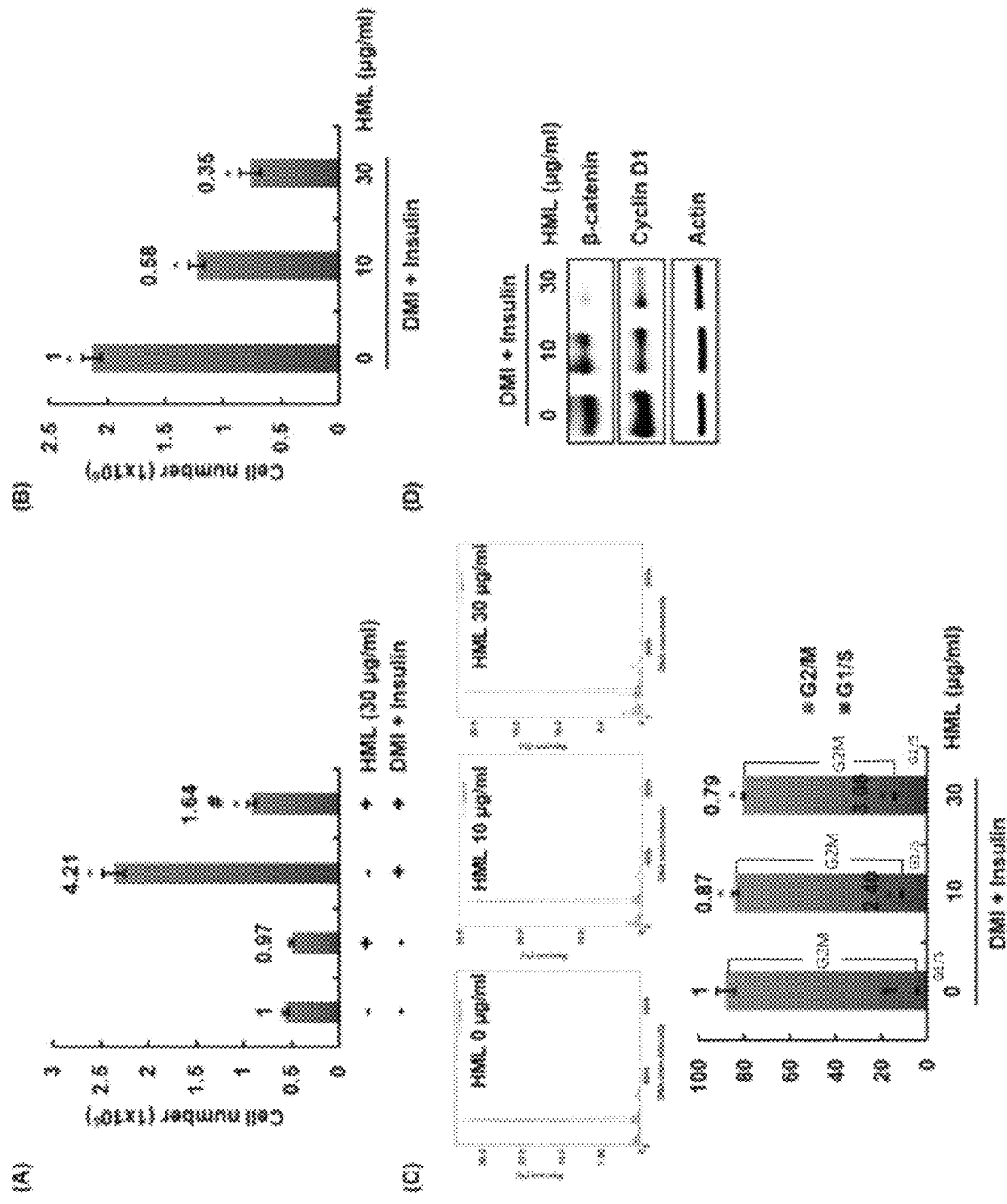
FIG. 2 is an image of Western blot results showing that a low-temperature extract of Geumhwagyu leaf (HML) inhibits the cell growth of mature adipocytes and suppresses the expression of β-catenin and cyclin D1, which are cell growth-related proteins.

In FIG. 2, a low-temperature extract of Geumhwagyu leaves (HML) obtained by extraction at 40° C. for 20 hours suggests inhibiting the cell growth of mature adipocytes and suppressing the expression of cell growth-related proteins β-catenin and cyclin D1.

Figure 3:
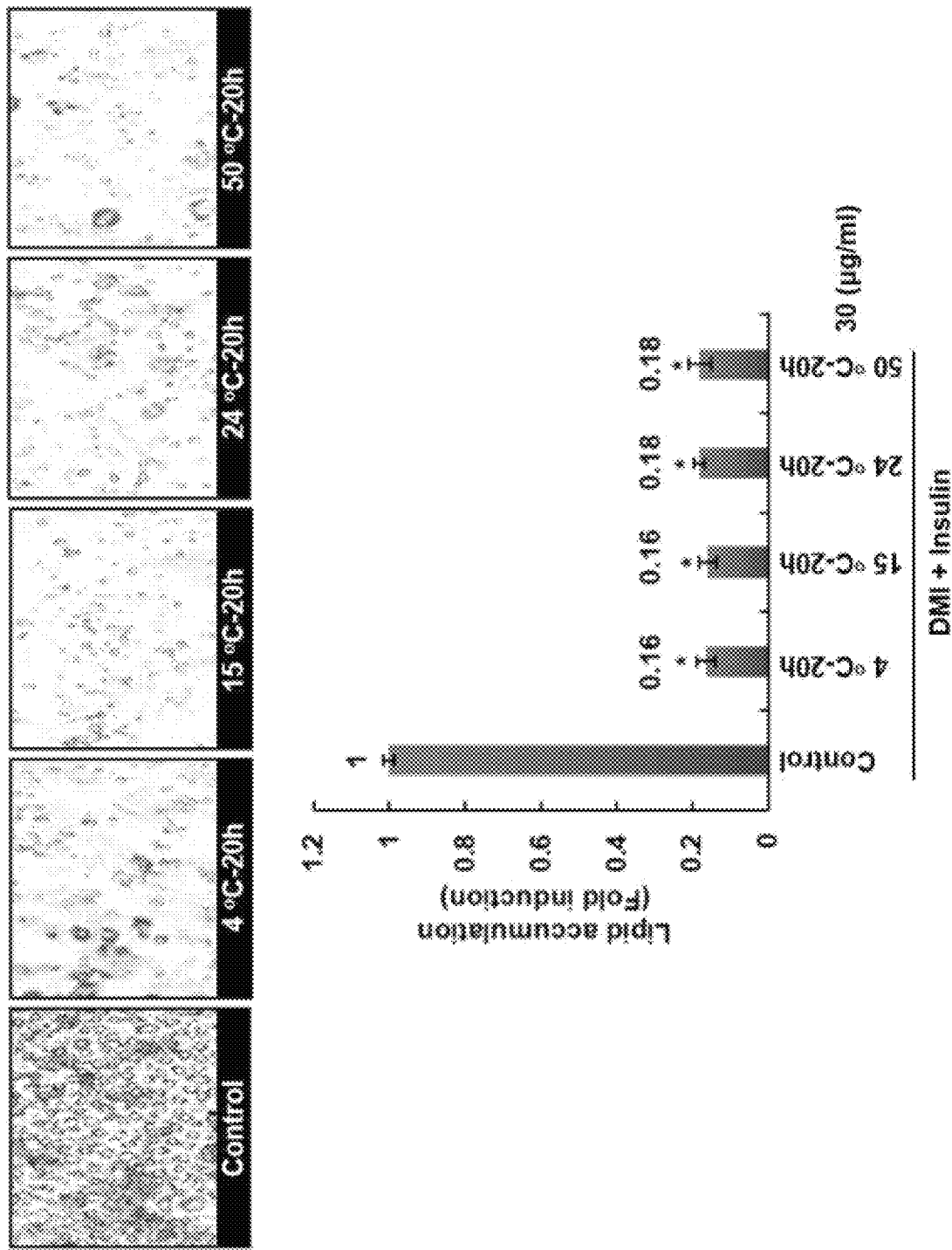
FIG. 3 is a graph showing the results of cell images and absorbance of cell eluate for lipid accumulation according to the Oil Red O experiment of Geumhwagyu leaf extract (HML) according to extraction temperature and extraction time conditions.
Figure 4:
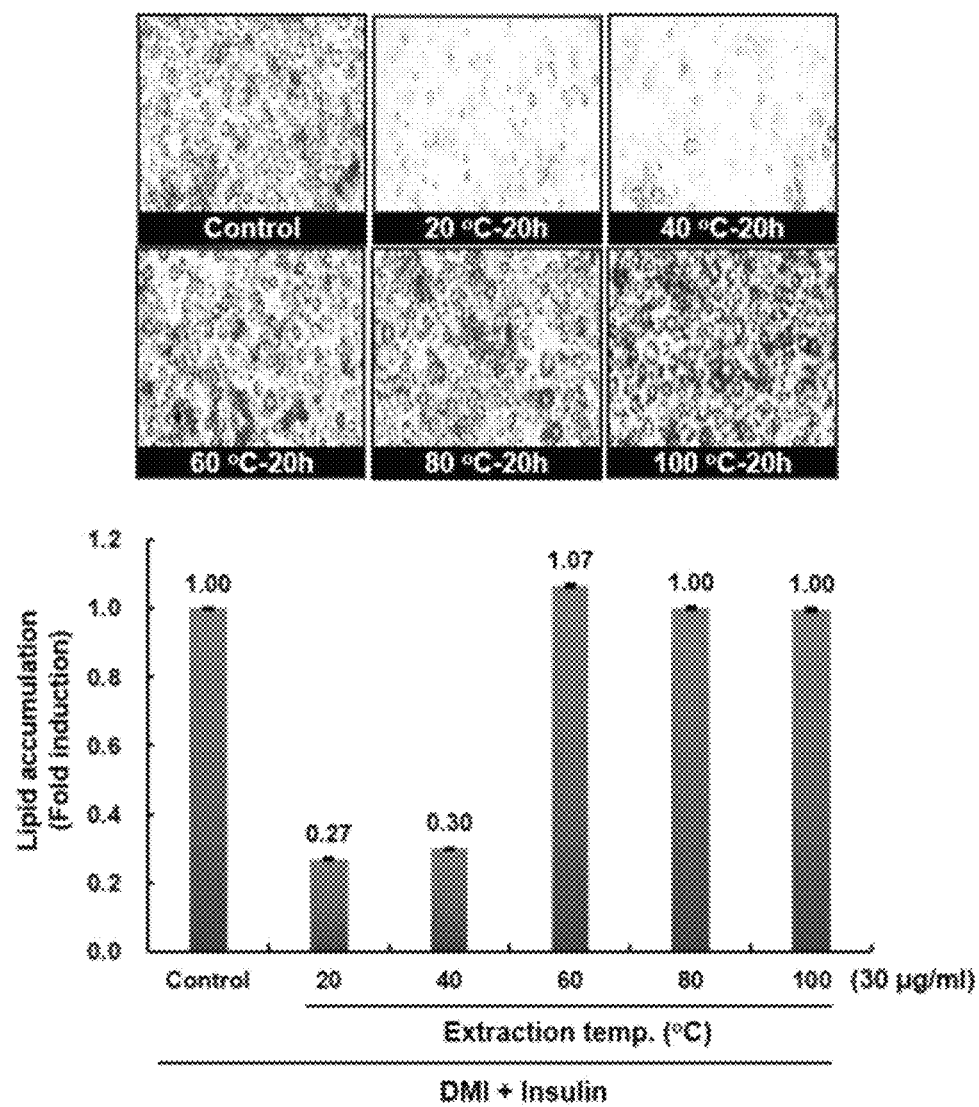
FIG. 4 is a graph showing the results of cell images and absorbance of the cell eluate for lipid accumulation according to the Oil Red O experiment of Geumhwagyu leaf extract (HML) extracted for 24 hours for each extraction temperature condition.
Figure 5:
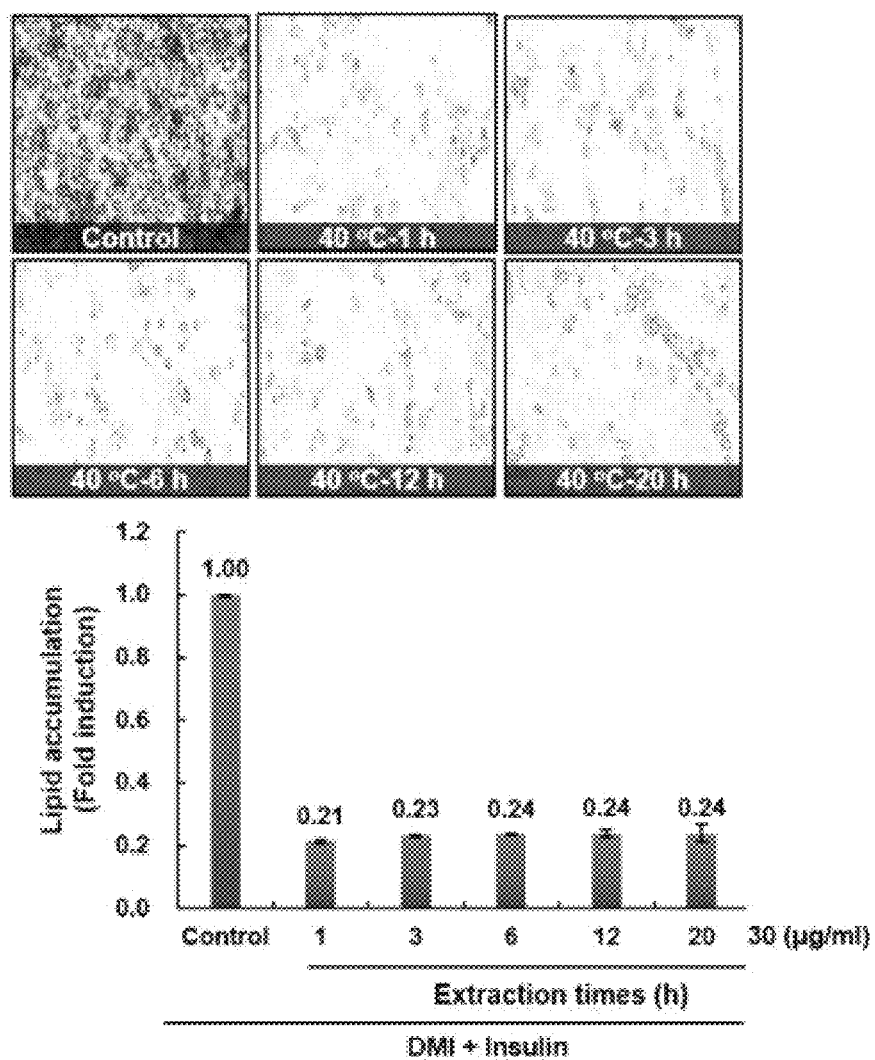
FIG. 5 is a graph showing the results of the cell image and the absorbance of the cell eluate for the lipid accumulation according to the Oil Red O experiment of the Geumhwagyu leaf extract (HML) extracted at 40° C. for each extraction time condition.

In FIG. 3, it can be confirmed the lipid accumulation inhibitory effect of the Geumhwagyu leaf extract (HML) according to extraction temperature and extraction time conditions. In FIG. 4, each extraction temperature condition, and in FIG. 5, each extraction time is confirmed in more detail. From these results, based on the cells induced to differentiate into adipocytes, Geumhwagyu leaf extract (HML) had an effect of inhibiting lipid accumulation by up to 88% at 30 µg/ml.

As described above, referring to FIGS. 1 to 5, it can be confirmed that each Geumhwagyu leaf extract inhibits lipid accumulation through the cell image, which is the result of the Oil Red O experiment, and the absorbance result of the cell eluate.

On the other hand, the ethanol aqueous solution extract and the methanol aqueous solution extract of the Geumhwagyu leaves were compared with the water extract of the Geumhwagyu leaves, and the experimental results of Oil Red O were compared in Tables 2 and 3. The ethanol aqueous solution extract and the methanol aqueous solution extract were prepared by extracting using ethanol and methanol as an extraction solvent instead of water, followed by distillation under reduced pressure.

TABLE 2

| Extract (40° C.) | Lipid accumulation (fold) Extract treatment concentration 30 µg/ml |
|---|---|
| Induction of fat differentiation | 1.00 |
| Fat differentiation induction + HML-water extract | 0.19 |
| Fat differentiation induction + HML-30 (v/v) % ethanol aqueous solution extract | 0.95 |
| Fat differentiation induction + HML-50 (v/v) % ethanol aqueous solution extract | 0.95 |
| Fat differentiation induction + HML-70 (v/v) % ethanol aqueous solution extract | 0.93 |

TABLE 3

| Extract (40° C.) | Lipid accumulation (fold) Extract treatment concentration 30 µg/ml |
|---|---|
| Induction of fat differentiation | 1.00 |
| Fat differentiation induction + HML-water extract | 0.17 |
| Fat differentiation induction + HML-30% (v/v) methanol aqueous solution extract | 0.92 |
| Fat differentiation induction + HML-50 (v/v) methanol aqueous solution extract | 0.93 |
| Fat differentiation induction + HML-70 (v/v) methanol aqueous solution extract | 0.96 |

Referring to Tables 2 and 3 above, the lipid accumulation effect is very excellent in the extract 30 µg/ml extracted with low-temperature water at 40° C. for 20 hours, but the lipid accumulation effect is very insignificant in the extract extracted with ethanol aqueous solution or methanol aqueous solution.

Through these results, it can be verified that the Geumhwagyu leaf extract has anti-obesity activity by increasing the energy consumption of adipocytes and enhancing energy metabolism.

Formulation Example 1. Pharmaceutical Preparations 200 g of the extract for each part of Geumhwagyu of the present disclosure was mixed with 175.9 g of lactose, 180 g of potato starch, and 32 g of colloidal silicic acid. After adding a 10% gelatin solution to this mixture, it was ground and passed through a 14 mesh sieve. This was dried, and 160 g of potato starch, 50 g of talc, and 5 g of magnesium stearate were added thereto, and the resulting mixture was made into tablets.

Formulation Example 2. Food Manufacturing

Formulation Example 2-1. Preparation of Cooking Condiments

Cooking condiments for health promotion were prepared by adding the extract of each part of Geumhwagyu of the present disclosure to the cooking condiments at 1% by weight.

Formulation Example 2-2. Flour Food Manufacturing

The extract for each part of Geumhwagyu of the present disclosure is added to wheat flour in an amount of 0.1% by weight, and the mixture is used to prepare bread, cake, cookies, crackers, and noodles to produce health-promoting food.

Formulation Example 2-3. Preparation of Soup and Gravies

The extract of each part of Geumhwagyu of the present disclosure was added to soup and gravies in an amount of 0.1% by weight to prepare health-promoting soup and gravies.

Formulation Example 2-4. Manufacture of Dairy Products

The extract of each part of Geumhwagyu of the present disclosure was added to milk in an amount of 0.1% by weight, and various dairy products such as butter and ice cream were prepared using the milk.

Formulation Example 2-5. Vegetable Juice Production

Vegetable juice for health promotion was prepared by adding 0.5 g of the extract of each part of Geumhwagyu of the present disclosure to 1,000 ml of tomato juice or carrot juice.

Formulation Example 2-6. Fruit Juice Manufacturing

Fruit juice for health promotion was prepared by adding 0.1 g of the extract for each part of Geumhwagyu of the present disclosure to 1,000 ml of apple juice or grape juice.

What is claimed is:
1. A tablet consisting essentially of a Geumhwagyu (*Hibiscus Manihot* L.) extract which is extracted using water of 4 to 50° C. as a solvent, polyvinyl pyrrolidone and microcrystalline cellulose.

* * * * *